United States Patent [19]

Yamauchi et al.

[11] 4,283,352
[45] Aug. 11, 1981

[54] METHOD FOR THE PRODUCTION OF α-TETRALONE

[75] Inventors: Takashi Yamauchi, Tokyo; Hirofumi Nanbu, Urawa, both of Japan

[73] Assignee: Kureha Kagaku Kogyo Kabushiki Kaisha, Tokyo, Japan

[21] Appl. No.: 800

[22] Filed: Jan. 3, 1979

Related U.S. Application Data

[63] Continuation-in-part of Ser. No. 817,597, Jul. 21, 1977, abandoned, which is a continuation of Ser. No. 703,776, Jul. 9, 1976, abandoned.

[30] Foreign Application Priority Data

Jul. 14, 1975 [JP] Japan .................................. 50/85242

[51] Int. Cl.$^2$ .................................................. C07C 45/02
[52] U.S. Cl. .................................... 568/311; 568/569; 568/328
[58] Field of Search ................................. 260/590 FA

[56] References Cited

U.S. PATENT DOCUMENTS

| | | | |
|---|---|---|---|
| 1,789,924 | 1/1931 | Binapfl et al. | 260/590 FA |
| 2,462,103 | 2/1949 | Johnson | 260/590 FA |

OTHER PUBLICATIONS

Robertson, J. Chem. Soc., vol. (1948), pp. 1574-1585.
Kharasch et al., J. Org. Chem., vol. 15, pp. 763-764, (1950).

*Primary Examiner*—Norman Morgenstern
*Assistant Examiner*—James H. Reamer
*Attorney, Agent, or Firm*—Stevens, Davis, Miller & Mosher

[57] ABSTRACT

In a method for the production of α-tetralone wherein tetralin is oxidized in the absence of a catalyst at a temperature of from 50° to 100° C. to an extent that the conversion of tetralin into tetralin hydroperoxide is 25 to 35 percent by weight, thereby producing a solution of tetralin hydroperoxide in tetralin, and wherein an inorganic metal salt is added to said solution to decompose the tetralin hydroperoxide to α-tetralone, the improvement comprising adding to said solution, as said inorganic metal salt, a mixture of at least one water-soluble inorganic iron salt and at least one water-soluble inorganic copper salt at a temperature of from 0° to 90° C.

4 Claims, 2 Drawing Figures

METHOD FOR THE PRODUCTION OF α-TETRALONE

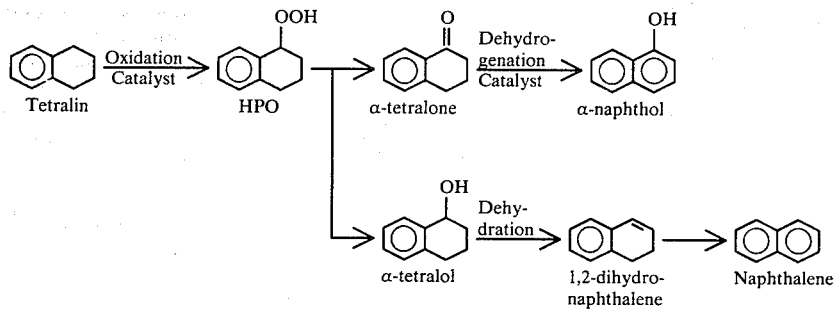

FIELD OF THE INVENTION

This is a continuation-in-part application of U.S. Patent application Ser. No. 817,597 filed on July 21, 1977 now abandoned which was filed as a Rule 60 continuation application Ser. No. 703,776 filed on July 9, 1976 now abandoned.

FIELD OF THE INVENTION

This invention relates to an improved method for the production of α-tetralone which is the raw material for α-naphthol.

BACKGROUND OF THE INVENTION

Heretofore, α-naphthol has been produced by a method which includes sulfonating naphthalene and subsequently subjecting the sulfonation product to alkali fusion. According to this method, however, β-naphthol is produced as by-product, which is recovered with the α-naphthol. Commercially, α-naphthol of high purity cannot be obtained by this method without difficulty. Recently, there has been proposed the so-called oxidation and dehydrogenation process as a method for the commercial production of α-naphthol of high purity. This oxidation and dehydrogenation process effects the production of α-naphthol by the steps of oxidizing tetralin to αtetralone in the presence of a catalyst and subsequently dehydrogenating the α-tetralone in the presence of a catalyst. This oxidation and dehydrogenation process, however, has the disadvantage that in the oxidation of tetralin performed in the presence of a catalyst, αtetralol occurs as a by-product and the amount of this by-product eventually affects the yield of α-naphthol. To be more specific, when tetralin is subjected to oxidation in the presence of a catalyst, the reaction produces tetralin hydroperoxide (hereinafter referred to as "HPO") as the intermediate, which immediately converts itself into α-tetralone and α-tetralol. The α-tetralone ane α-tetralol have close boiling points and, therefore, cannot be separated from each other without difficulty. In the dehydrogenation of α-tetralone in the presence of a catalyst in this process, therefore, it is actually the mixture of α-tetralone and α-tetralol that undergoes the treatment for dehydrogenation. In the dehydrogenation, α-tetralol is dehydrogenated to 1,2-dihydronaphthalene and this 1,2-dihydronaphthalene undergoes further dehydrogenation to naphthalene. It follows that in the oxidation and dehydrogenation process, the amount of naphthalene increases and the yield of α-naphthol consequently decreases in proportion as the α-tetralol content increases in the mixture of α-tetralone and α-tetralol. The reaction mechanism which is involved in the oxidation and dehydrogenation process is indicated below.

It has been customary in this oxidation and dehydrogenation process to resort to extensive use as a catalyst a metal salt of an organic compound such as iron naphthenate or cobalt naphthenate. When such an organic metal salt is used as the catalyst, however, since the oxidation of tetralin is carried out at temperatures of 120° to 130° C., the HPO occurring as the intermediate in this reaction readily undergoes conversion into α-tetralol. Further at this temperature level, part of the α-tetralol thus produced undergoes dehydration.

In view of the above circumstances, attempts have been made to improve the catalyst in the oxidation of tetralin with a view toward lowering the α-tetralol content in admixture with α-tetralone.

U.S. Pat. No. 2,462,103 by Johnson et al. discloses the process comprising controllably oxidizing tetralin with air or oxygen in the presence or absence of catalyst in such manner as to form a maximum proportion of HPO and decomposing catalytically the formed HPO with an aqueous solution of a copper salt of a mineral acid.

This process has, however, an unsatisfactory results because the percentage of decomposition of HPO is not more than 90% and the highest ratio of α-tetralone/α-tetralol obtained by the decomposition, namely the selectivity to α-tetralone over α-tetralol, is only the order of 15/1.

The article by Kharash et al., J. Org. Chem., vol. 15, pages 763–774(1950), discloses a process of decomposing HPO in the presence of ferrous ammonium sulfate in a nonaqueous solution, ethanol. This process of Kharash et al. disappointingly results in the low ratio of α-tetralone to α-tetralol of at most about 10/1 and in the formation of an unwanted by-product, α-alkoxynaphthalene, besides α-tetralol.

SUMMARY OF THE INVENTION

An object of the present invention, therefore, is to provide a method whereby α-tetralone useful advantageously produced from tetralin with a substantially complete decomposition of HPO and a predominantly high selectivity to α-tetralone product.

This and other objects to the present invention will become apparent from the description given below.

The present invention is the result of a study in search of conditions under which possible conversion to α-tetralol of the HPO intermediate in the oxidation of tetralin is impeded and conditions under which quick conversion of the HPO into α-tetralone are obtained.

The present invention provides a method for the production of α-tetralone, which includes oxidizing tetralin into HPO in the absence of a catalyst at temperatures of 50 to 100° C. to an extent such that the conversion of tetralin to HPO falls in the range of 25 to 35 percent by weight, and then adding to the resultant tetralin solution a catalyst consisting of a mixture of at least one water-soluble inorganic iron salts and at least one water-soluble inorganic copper salts at a temperature of from 0° to 90° C., thereby almost completely decomposing the formed HPO to α-tetralone with high yield or selectivity.

DETAILED DESCRIPTION OF THE INVENTION

In the present invention, the first step is to oxidize tetralin in the absence of a catalyst to produce HPO, which oxidation may be effected with oxygen or air. The temperature at which the oxidation is effected is from 50° to 100° C., preferably from 70° to 90° C. This oxidation must be controlled so that the conversion of tetralin to HPO falls in the range of 25 to 35 percent by weight, preferably from 25 to 30 percent by weight.

Figure 1:
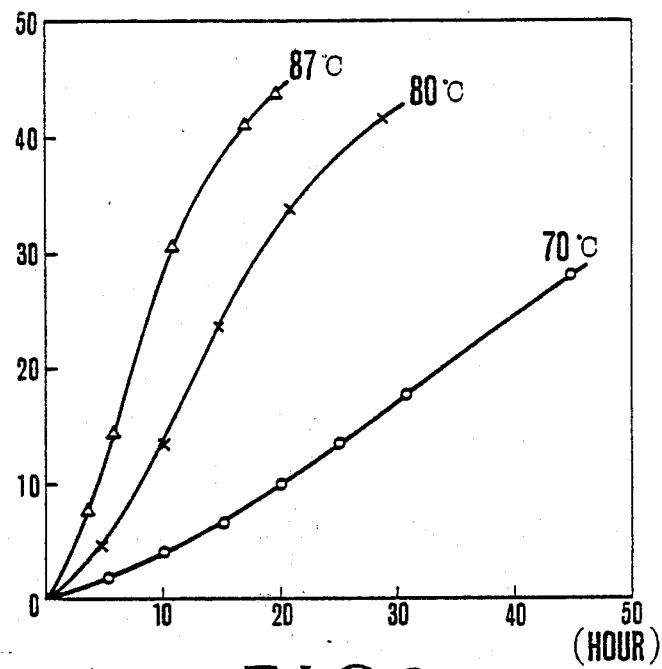
FIG. 1 is a graph showing the velocities of oxidation of tetralin in the absence of a catalyst for conversion to HPO at the various temperatures indicated.

FIG. 1 is a graph showing the velocities of oxidation of tetralin in the absence of a catalyst at various temperatures to form HPO. In FIG. 1, the vertical axis represents the amount of HPO (in percent by weight) produced and the horizontal axis represents the time (in hours) of the oxidation reaction. It is clear from FIG. 1 that, at each of the temperatures, the oxidation of tetralin begins to proceed at an increased rate after elapse of a certain induction period (about 30 minutes) and that the velocity of the reaction of oxidation increases substantially at a linear rate until the amount of HPO produced (concentration of formed HPO in the tetralin) reaches 30 to 35 percent by weight. It is also seen, however, that the velocity of the reaction of oxidation gradually dwindles apparently after the amount of HPO produced passes 30 percent by weight. A possible reason for this may be that a secondary reaction begins to occur within the reaction system. For the purpose of retaining the formed HPO in its unaltered form, therefore, it becomes necessary to control the oxidation of tetralin in such way that the amount of formed HPO may remain below 35 percent by weight, preferably to fall in the range of 25 to 30 percent by weight. Thus the duration of the reaction and the reaction temperature must be properly coordinated. If the reaction temperature falls below 50° C., then the velocity of the reaction of oxidation becomes too slow for the reaction to be practically feasible. It is, therefore, necessary that the oxidation of tetralin should be carried out at temperatures of not less than 50° C.

Figure 2:
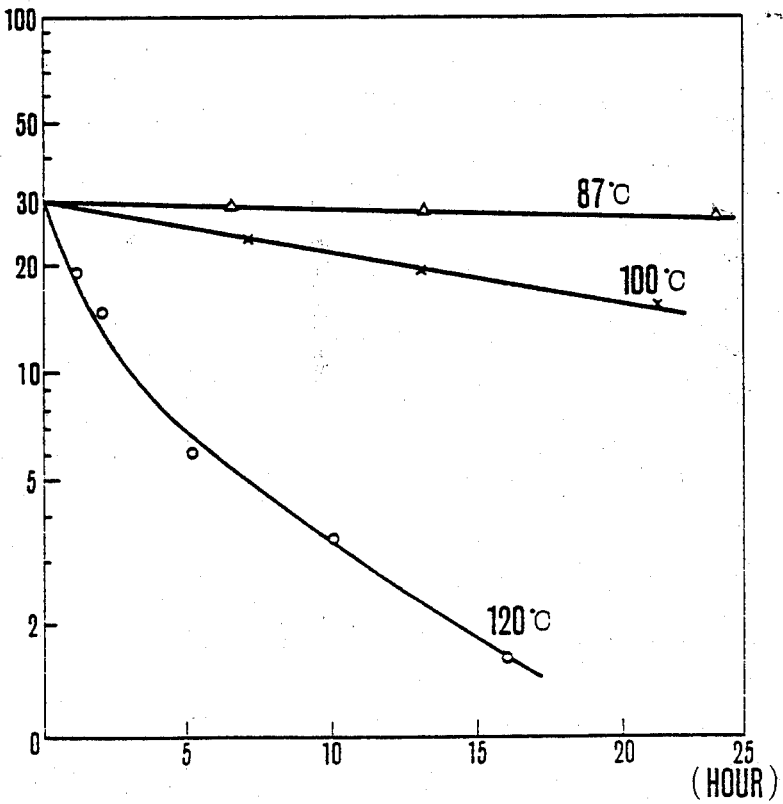
FIG. 2 is a graph showing changes of the HPO concentration in the tetralin solution as determined by heating the tetralin solution containing HPO at an initial concentration of 30 percent by weight at the various temperatures indicated.

FIG. 2 is a graph showing changes of HPO concentration in the tetralin solution as determined by heating the tetralin solution containing HPO at an initial concentration of 30 percent by weight at the various temperatures indicated. In FIG. 2, the vertical axis represents the amount (in percent by weight) of HPO remaining in the tetralin solution and the horizontal axis represents the duration (in hours) of heating. It is evident from FIG. 2 that when the temperature of heating is 87° C. or under, the conversion of HPO to any other substance (the percentage of HPO to be converted to α-tetralone and α-tetralol) is extremely low. Under the conditions of 87° C. and 10 hours, for example at least 98 percent by weight of the formed HPO is retained in its unaltered form in the tetralin solution. As the temperature rises past 100° C., the conversion of HPO to other substances shows a notable increase. Under 120° C. for 10 hours, for example, the formed HPO is substantially conveted.

As is plain from the foregoing explanation of FIG. 1 and FIG. 2, it is necessary for the purpose of this invention that the oxidation of tetralin for conversion into HPO should be carried out in the absence of a catalyst at temperatures of 50° to 100° C. to an extent such that the conversion of tetralin to HPO falls in the range of 25 to 35 percent by weight, preferably 25 to 30 percent by weight.

In the next step of the present invention, the catalyst consisting of a Mixture at least one water-soluble inorganic iron salts and at least one water-soluble inorganic copper salts is added at a temperature of from 0° to 90° C., preferably from 0° to 50° C., to the tetralin solution containing the HPO, formed therein as described above, at a concentration of 25 to 35 percent by weight, preferably from 25 to 30 percent by weight. Examples of the inorganic iron salt suitable for this purpose include ferrous sulfate, ferrous ammonium sulfate, ferrous chloride, ferric chloride, ferrous nitrate and ferric nitrate. Examples of the inorganic copper salt suitable for this purpose include cuprous chloride, cupric chloride and cupric sulfate. The catalyst according to this invention increases the velocity of the conversion of HPO to α-tetralone.

A sufficient amount of the catalyst ranges from 1 mol equivalent to 1/50 mol (as metal), preferably from $\frac{1}{2}$ mol to 1/30 mol, per mol of the HPO present in the solution. If the catalyst is added in an amount greater than 1 mol equivalent, the excess amount added does not bring about any enhancement in the effect. If it is added in an amount smaller than 1/50 mol, virtually no effect can be expected. Thus, the proper amount falls in the range mentioned above. The molar ratio of iron salt to copper salt in the catalyst consisting of the mixture of metal salts according to this invention may be properly determined so as to most effectively decompose HPO to α-tetralone, for instance the ratio of iron salt/copper salt usually ranges from about 1/10 to 10/1. The amount of iron salt in the mixture preferably ranges over 0.03 mol per mol of the HPO present in the solution.

The addition of the mixture of metal salts to the terralin solution may conveniently be accomplished by dissolving the inorganic metal salt in water to produce an aqueous solution and adding this aqueous solution to the tetralin solution. The temperature at which the mixture of metal salts is added to the tetralin solution as described above is in the range of from 0° to 90° C., preferably from 0° to 50° C.

If this temperature is higher than the upper limit 90° C., then the conversion of HPO into α-tetralol becomes conspicuous and thus the temperature must be kept from rising above 90° C. This temperature is preferred to be low because the reaction for the conversion of HPO to α-tetralone proceeds with an evolution of heat. A temperature below 0° C. is not satisfactory, for at such a low temperature, the conversion of HPO does not proceed. When the temperature at the decomposition of HPO is maintained in the range specified above, HPO is almost completely coverted into α-tetralone with an extremely high selectivity. The ratio of α-tetralone to α-tetralol obtained by the method of the present invention results more than about 30.

Thus, a tetralin-water mixture containing α-tetralone is obtained by treating tetralin by the method of this invention as described above. From this mixture, α-teteralone can be obtained by simply subjecting the mixture to ordinary fractionation. This is accomplished, for example, by freeing the mixture from the precipitate by sedimentation, separating the resultant mixture into a water phase and an oil phase, and separating α-tetralone from the oil phase by fractional distillation. The tetralin which is recovered in this manner may be used again as the raw material for the production of α-tetralone by this invention or may be put to some other suitable use.

The present invention will be described more specifically below with reference to preferred embodiments, which are given solely for illustration and should not be considered as limitations of the invention.

EXAMPLE 1

In a cylindrical glass reactor, 500 g of commercial tetralin was placed. Oxygen delivered through a glass filer upwardly through the bottom of the cylinder at 87° C. at a flow rate of 20 liters/hour for 11 hours. Consequently, the tetralin was converted into a tetralin solution containing 30 percent by weight of HPO. The HPO content of this solution was determined by iodometry. Then, 1.5 g of ferrous sulfate ($FeSO_4.7H_2O$) and 0.2 g of cuprous chloride (CuCl) were dissolved in 100 ml of water. The resultant aqueous solution was placed in a flask and a part, 100 g, of the tetralin solution of 30% HPO was added dropwise to the aqueous solution over a period of two hours. In this case, the molar ratio of HPO/Fe/Cu was 1/0.03/0.01. In this reaction, the flask was cooled with ice so that the reaction temperature remained in the range of 5° to 10° C. After the dropwise addition, the mixture was agitated for 30 minutes, thereafter centrifugally sedimented and freed from the sediment. The resultant mixture was sedimented into a water phase and an oil phase and the oil phase was gas chromatographically analyzed with the following results.

| HPO | 0.2 percent by weight |
| α-Tetralone | 25.9 percent by weight |
| α-Tetralol | 0.7 percent by weight |
| 1,2-Dihydronaphthalene | 0.2 percent by weight |
| α-Tetralone/α-tetralol | 37/1 percent by weight |

As is clear from the results above, the formed HPO was decomposed almost completely and the product ratio of α-tetralone to α-tetralol, namely the selectivity of α-tetralone product, was much greater than the heretofore attainable ratio of about 15.

By way of comparison, the procedure of Example 1 was repeated, except for omission of the addition of cuprous chloride. In the reaction, the concentration of the remaining HPO in the solution was still 9.4 percent by weight when 10 hours passed after completion of the dropwise addition of tetralin solution, illustrating the effect of the combined use of the two inorganic metal salts.

EXAMPLE 2-13

Example 1 was repeated in Example 2-13 with the exception of changing the contents of the catalyst, the temperature at the decomposition of HPO and the period for adding the oxidized tetralin solution.

The results of these examples were indicated in Table 1.

The effectiveness of the present invention is shown in Table 1, that is while the heretofore attainable rate of decomposition of HPO has been at most about 90%, the rate of decomposition of HPO according to the method of the present invention is nearly complete and moreover, the ratio of α-tetralone to α-tetralol according to the method of the present invention becomes more than about 30. When the value of more than about 30 of the ratio is compared to at most 15 of the heretofore attainable value of the ratio, it is seen that the selectivity of the method of the present invention in giving α-tetralone is extremely higher than those in the past.

TABLE 1

| | | | | | | | results | | | | |
|---|---|---|---|---|---|---|---|---|---|---|---|
| Ex | catalyst and amount thereof | concentration of HPO | molar ratio of cat/HPO | molar ratio of Fe/Cu | molar ratio of HOP/Fe/Cu | Temp. (°C.) | Time (hr) | residual HPO (wt %) | α-tetralone (wt %) | α-tetralol (wt %) | 1,2-dihydronaphthalene (wt %) | α-tetralone/α-tetralol |
| 2 | $FeSO_4.7H_2O$ 25.0 gr(0.09 mole) $CuCl_2$ 12.1 gr(0.09 mole) | 30% (0.183 mole) | 1/1 | 1/1 | 1/0.5/0.5 | 0-5 | 2.5 | <0.1 | 28.0 | 0.7 | 0.1 | 40/1 |
| 3 | $FeSO_4.7H_2O$ 1.5 gr(5.5×10$^{-3}$ mole) $CuCl_2$ 0.24 gr(1.8×(1.8×10$^{-3}$ mole) | 30% (0.183 mole) | 0.04/1 | 3/1 | 1/0.03/0.01 | 0-5 | 2.5 | <0.1 | 28.1 | 0.67 | <0.1 | 42/1 |
| 4 | $FeSO_4(NH_4)_2SO_4.6H_2O$ 1.67 gr(0.006 mole) CuCl 0.59 gr(0.006 mole) | 30 | 0.066/1 | 1/1 | 1/0.33/0.033 | 50 | 2.5 | 0.1 | 26.3 | 0.8 | 0.1 | 33/1 |
| 5 | $FeSO_4.7H_2O$ 4.24 gr(0.01524 mole) $CuSO_4.5H_2O$ 7.62 gr(0.03048 mole) | 24 | 0.3/1 | 1/2 | 1/0.1/0.2 | 20 | 1.0 | <0.1 | 22.1 | 0.63 | <0.1 | 35/1 |
| 6 | $FeCl_2.4H_2O$ | | | | | | | | | | | |

TABLE 1-continued

| Ex | catalyst and amount thereof | concentration of HPO | molar ratio of cat/HPO | molar ratio of Fe/Cu | molar ratio of HOP/Fe/Cu | Temp. (°C.) | Time (hr) | residual HPO (wt %) | α-tetralone (wt %) | α-tetralol (wt %) | 1,2-dihydronaphthalene (wt %) | α-tetralone/α-tetralol |
|---|---|---|---|---|---|---|---|---|---|---|---|---|
|  | 14.57 gr(0.0732 mole) CuCl$_2$ . 2H$_2$O 3.12 gr(0.0183 mole) | 30 | 0.5/1 | 4/1 | 1/0.4/0.1 | 0-5 | 2.5 | 0.1 | 26.9 | 0.7 | <0.1 | 38/1 |
| 7 | Fe(NO$_3$)$_3$ . 9H$_2$O 29.57 gr(0.0732 mole) 3.12 gr(0.0183 mole) | 30 | 0.5/1 | 4/1 | 1/0.4/0.1 | 0-5 | 2.5 | 0.2 | 26.8 | 0.8 | 0.1 | 34/1 |
| 8 | FeSO$_4$ . 7H$_2$O 20.35 gr(0.0732 mole) CuCl$_2$ 2.46 gr(0.0183 mole) | 30 | 0.5/1 | 4/1 | 1/0.4/01 | 20-25 | 1.5 | 0.2 | 26.7 | 0.7 | 0.2 | 38/1 |
| 9 | FeSO$_4$ . 7H$_2$O 1.70 g(0.0061 mole) CuCl$_2$ 8.2 gr(0.061 mole) | 25 | 0.44/1 | 1/10 | 1/0.04/0.4 | 20 | 1.0 | 0.2 | 21.5 | 0.73 | 0.1 | 29/1 |
| 10 | FeSO$_4$ . 7H$_2$O 13.9 gr(0.05 mole) FeSO$_4$ . (NH$_4$)$_2$SO$_4$ . 6H$_2$O 19.6 gr(0.05 mole) CuSO$_4$ . 5H$_2$O 2.5 gr(0.01 mole) | 30 | 0.11/1 | 10/1 | 1/0.1/0.01 | 20-25 | 1.0 | <0.1 | 27.0 | 0.8 | 0.1 | 34/1 |
| 11 | FeCl$_3$ . 6H$_2$O 1.73 gr(0.0064 mole) FeCl$_2$ . 4H$_2$O 1.27 gr(0.0064 mole) CuCl 0.54 gr(5.5×10$^{-3}$ mole) | 30 | 0.1/1 | 7/3 | 1/0.07/0.03 | 40-45 | 2.5 | 0.2 | 26.1 | 0.8 | 0.1 | 33/1 |
| 12 | FeSO$_4$ . 7H$_2$O 1.7 gr(0.0061 mole) CuSO$_4$ . 5H$_2$O 2.29 gr(0.0091 mole) | 25 | 0.1/1 | 2/3 | 1/0.04/0.06 | 20 | 1.0 |  | 21.6 | 0.71 | 0.1 | 30/1 |
| 13 | FeSO$_4$ . 7H$_2$O 0.42 gr(0.001524 mole) CuSO$_4$ . 5H$_2$O 3.81 gr(0.01524 mole) | 25 | 0.11/1 | 1/10 | 1/0.01/0.1 | 85 | 1.0 | 0.3 | 21.0 | 1.0 | 0.2 | 21/1 |

What is claimed is:

1. A method for the production of alpha-tetralone comprising:
 oxidizing tetralin in the absence of any catalysts at a temperature of from 50° to 100° C. to an extent that the conversion of tetralin into tetralin hydroperoxide is 25 to 35% by weight, thereby producing a solution of tetralin hydroperoxide in tetralin; and decomposing the thus formed tetralin hydroperoxide into alpha-tetralone at a temperature of from about 0° to 90° C. in the presence of an added catalyst to the solution thus obtained, which catalyst comprises a mixture of (1) an iron salt selected from the group consisting of ferrous sulfate, ferrous ammonium sulfate, ferrous chloride, ferric chloride, ferrous nitrate and ferric nitrate, and (2) a copper salt selected from the group consisting of cuprous chloride, cupric chloride and cupric sulfate, the molar ratio of the iron salt to the copper salt in the mixture being in the range of from 0.1 to 10.

2. The method according to claim 1 wherein the catalyst is added to the solution of tetralin hydroperoxide in tetralin in an amount of one equivalent mole to 1/50 mole (as metal) per mole of tetralin hydroperoxide present in the solution.

3. The method according to claim 1 wherein the decomposition of the tetralin hydroperoxide is carried out at a temperature of from 0° to 50° C.

4. The method according to claim 2 wherein the amount of the catalyst is in the range of 1/30 to ½ mole (as metal) per mole of tetraline hydroperoxide.

* * * * *